United States Patent [19]

Lee

[11] Patent Number: 4,721,463
[45] Date of Patent: Jan. 26, 1988

[54] INTERCHANGEABLE DENTAL ARTICULATORS

[76] Inventor: Robert L. Lee, 22575 Barton Rd., Grand Ter., Colton, Calif. 92324

[21] Appl. No.: 913,727

[22] Filed: Sep. 30, 1986

[51] Int. Cl.$^4$ .............................................. A61C 11/00
[52] U.S. Cl. ......................................... 433/54; 433/56
[58] Field of Search ....................... 433/54, 55, 56, 57, 433/58, 61

[56] References Cited

U.S. PATENT DOCUMENTS

| | | | |
|---|---|---|---|
| 1,670,311 | 5/1928 | Musante | 433/55 |
| 4,352,662 | 10/1982 | Lee | 433/56 |
| 4,496,319 | 1/1985 | Stienbock | 433/56 |

*Primary Examiner*—Robert Peshock
*Attorney, Agent, or Firm*—Knobbe, Martens, Olson & Bear

[57] ABSTRACT

A dental articulator is formed by mounting upper and lower frames of an articulator on a precisely formed alignment block. Condylar elements are captured by fixtures attached to the upper frame, while pedestals for the condylar elements have their lower ends extending into flowable bonding material positioned in sockets in the upper frame. The bonding material sets while the condylar elements are precisely held by the upper frame.

16 Claims, 9 Drawing Figures

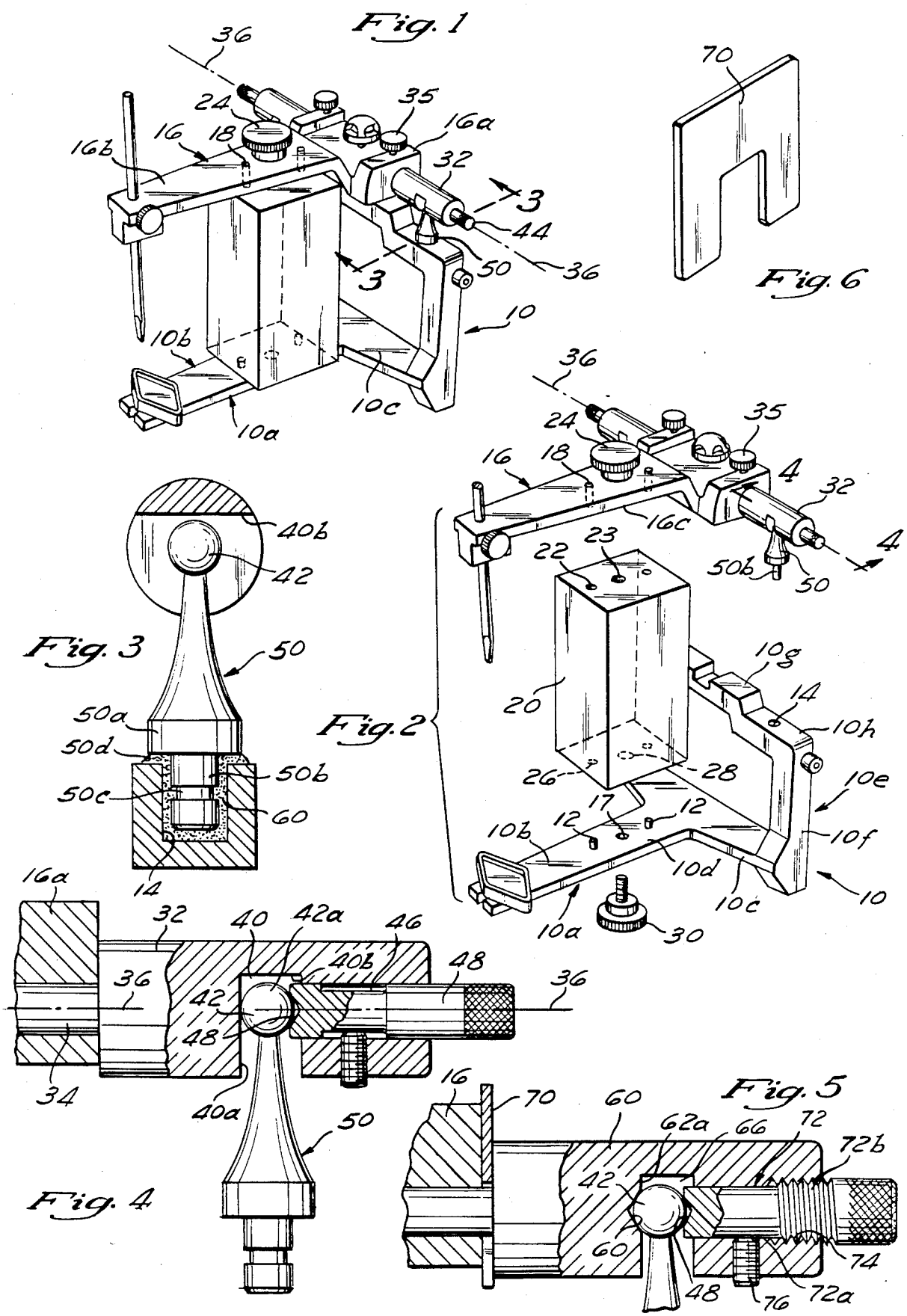

INTERCHANGEABLE DENTAL ARTICULATORS

FIELD OF THE INVENTION

This invention relates to dental apparatus, and more particularly, to an improved method of making dental articulators and to the resulting improved apparatus.

BACKGROUND OF THE INVENTION

A significant amount of dentistry is done by the indirect method in which models or casts of the patient's upper and lower tooth structures are mounted on a dental articulator which has hinged frames that may be moved in a manner to simulate jaw movement. Great strides have been made in the taking and recording of jaw movement measurements and other information. This, in turn, increases the accuracy of the dental casts made from this information and ultimately effects the accuracy of the resulting jaw movement simulation when the casts are mounted on a dental articulator.

Typically, a dentist or his assistant will take a mold of the patient's teeth and then give the mold to a lab technician for the preparation of the dental cast. These models or dental casts are mounted on plates in an articulator in the laboratory. The casts are usually later transmitted to the dentist or orthodontist who uses them in an articulator in his office or work area, which is normally in a different location. The casts are usually used considerably when initially made, and then they are normally stored but used at later times as well.

The accuracy of the conclusions based on the jaw movement simulation with those models is dependent upon many factors. One such factor is the accuracy of the articulator itself. It is desirable that articulators of a given type be manufactured with sufficient accuracy and consistency that they are interchangeable. This enables dental casts first mounted in one articulator at one time to be used later on a different articulator at another time.

Various techniques have been utilized to improve the accuracy in the manufacture of articulators. Certain manufacturers of articulators attempt to overcome the interchangeability problem by providing auxiliary equipment such as binoculars and crosshairs in order to accurately adjust the mounting of a cast in an articulator to eliminate the effort of dimensional irregularities. These devices however, are costly and require considerable time in use.

In another approach set forth in U.S. Pat. No. 4,352,662, accuracy is obtained by recognizing the importance of certain relationships articulator frames and then using alignment blocks and extreme care in machining of the articulator frames. Naturally, as tolerance requirements are increased, the costs of machining are increased or else the quality control rejection rate is increased. In spite of these advances in accuracy and interchangeability, a need still exists for improvements in accuracy and in the cost of manufacture of dental articulators.

SUMMARY OF THE INVENTION

In accordance with the method of the invention, a pair of sockets are formed in the upper surface of a vertical support portion of the lower frame of a dental articulator. These sockets are spaced from each other on opposite sides of the support and are adapted to receive the lower ends of pedestals on support posts, each having a condylar element on its upper end. The sockets are larger than the lower ends of the pedestals posts. The upper frame of a dental articulator is then positioned above the lower frame in a predetermined known precise position. This position is preferably that corresponding to the centric position when the articulator is completed and assembled.

Preferably, the frames are placed in this predetermined position by accurately forming a mounting area on each frame for receiving a dental cast mounting plate and then positioning a precisely formed alignment block between the frames with the ends of the block engaging said mounting plate areas. The alignment block ends engaging the frames have a precisely known relationship such as being precisely parallel to each other and being at a precisely known height.

The method further comprises capturing a pair of the condylar elements in fixtures carried on the upper frame such that the condylar elements define a hinge axis for the articulator. This axis is precisely parallel to the mounting areas on the frames. Preferably, this is accomplished by drilling holes in the upper frame on this same axis, and positioning mounting shafts attached to the fixture in these holes. The condylar elements, attached to the pedestals, are to be connected to the lower frame of the articulator. This connection is accomplished by placing quick-setting, flowable, bonding material into the sockets in the lower articulator frame. The lower ends of the support pedestals are positioned into the bonding material in the sockets as the upper frame is placed into its predetermined position with respect to the lower frame on the alignment block. This position is such that the ends of a condylar pedestal are suspended within the sockets, but are unrestrained by the sockets so that the accuracy of the relation between the condylar elements and the upper frame is not disturbed. The frames are then held in this position while the bonding material hardens. In this way, the accurate relation between the condylar elements and the upper frame is maintained as the pedestals and hence the condylar elements are secured to the lower frame.

In use of the articulator, the condylar elements are released from the fixtures on the upper frame and these fixtures are replaced by guides used for simulating jaw movement. Further, the frames are disconnected from the alignment block and dental cast mounting plates are secured to the articulator frames in the area in which the alignment block ends were attached.

The apparatus of the invention comprises the articulator made by the method of the invention. This includes an articulator frame having sockets in its vertical support portion which are oversized with respect to the ends of condylar pedestals positioned in the sockets. A layer of quick-setting bonding material positions the ends of the pedestals with respect to the lower support frame and forms the only interconnection between the pedestals and the support frames. The pedestals have enlarged bases adjacent their lower ends, with these bases having a diameter greater than the diameter of the sockets. Howver, the lower surfaces of the support bases are actually spaced from the frame by a layer of bonding material which further connects the pedestals to the frame. With this approach, the frame surface accuracy is not critical just as the diameter of the sockets therein is not. Instead, the accuracy is obtained directly through the condylar element and the upper frame.

DESCRIPTION OF THE DRAWINGS

FIG. 1 is a perspective view of a dental articulator being made in accordance with the method of the invention.

FIG. 2 is an exploded perspective view of the elements of FIG. 1 illustrating the manner in which the articulator frames are mounted on the alignment block and the manner in which the condylar elements are suspended by the upper frame.

FIG. 3 is an enlarged, cross-sectional view on line 3—3 of FIG. 1, illustrating the manner by which the condylar pedestals are secured to the lower frame.

FIG. 4 is an enlarged, cross-sectional view on line 4—4 of FIG. 2, illustrating the manner in which the condylar elements are secured by the upper frame.

FIG. 5 is a cross-sectional view similar to that of FIG. 4, but illustrating a further embodiment of the invention.

FIG. 6 is a perspective view of a shim used in the embodiment of FIG. 5.

DETAILED DESCRIPTION OF THE INVENTION

Figure 7:
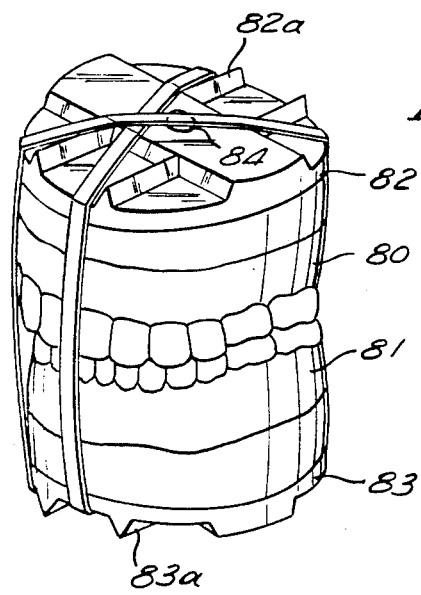
FIG. 7 is a perspective view of pair of dental casts as they are typically mounted when being stored or transferred from one articulator to another.

Referring first to FIGS. 1 and 2, there is illustrated the lower frame 10 of a dental articulator, with such frame including a generally horizontal T-shaped base member 10a having a forwardly extending arm 10b and a rear crossbar 10c. Accurately formed or machined on the arm 10b is a mounting ara 10d, which is the area for receiving a dental cast mounting plate when the finished articulator is in use. A pair of precisely positioned alignment dowels 12 are positioned in the lower frame arm 10b extending upwardly from and perpendicular to the surface 10d in spaced parallel relation.

The lower frame 10 is further provided with a rear vertical support bridge 10e having two posts 10f which are connected at their lower ends to the ends of the crossbar 10c and at their upper ends to the ends of a truss 10g to form a closed loop. Formed in the upper surface 10h of the truss 10g are a pair of spaced sockets 14, one of which is shown in FIG. 2. The other one (not shown) is located on the opposite side of the frame positioned symmetrically with respect to the one shown.

Also shown in FIGS. 1 and 2 is an upper articulator frame 16 having a rear portion 16a and a forwardly extending arm 16b similar to the forward arm 10b on the lower frame. The lower surface of this forward arm 16b includes an accurately machined area 16c for receiving a dental cast in a finished articulator. A pair of precisely positioned spaced, alignment dowels 18 extend downwardly from and perpendicular to this dental cast mounting plate area 16c.

In accordance with the invention, the frames are held in a precise predetermined position by means of a alignment block 20 having its upper and lower surfaces precisely machined parallel to each other. The alignment block upper surface is provided with a pair of precisely formed sockets 22 for receiving the dowels 18, and a centrally located threaded opening 23 for receivein the mounting screws 24 extending through the upper frame. The lower surface of the alignment block 20 is similarly provided with a pair of precisely formed alignment sockets 26 for receiving the dowels 12. It is further formed with a centrally located threaded opening 28 for receiving a mounting screw 30 which extends through the opening 17 in the lower frame arm 10b and threads into the opening 28 in the lower surface of the alignment block 20. The alignment block holds the precisely machined surfaces 10d on the lower frame and 16c on the upper frame in parallel relation to each other.

A pair of fixtures or guides 32 are mounted on shafts 34 that extend into the rear frame central portion 16a, as further seen from FIG. 4. The mounting holes for the shafts 34 are precisely formed in a colinear manner to define a hinge axis 36 for the articulator. This axis is precisely parallel to the upper frame surface 16c, and also parallel to the lower frame surface 10d, when the articulator frames are mounted on the alignment block, as shown in FIG. 1. The shaft 34 is held within the frame portion 16a by suitable set screws 35.

The fixtures 32 are cylindrical members which include a downwardly open space or cut-out 40, as seen in FIG. 4. A spherical condylar element 42 is positioned in each space 40 and captured in that space between cut out wall 40a and a retainer pin 44 which extends through a bore in the outer end of the fixture 32. The axis of the bore 46 is precisely colinear with the axis 36 for the shaft 34 and this axis 36 extends through the center 42a of the condylar element 42. The retaining pin 44 fits precisely and snugly within its mating bore. Each pin 44 is held within its bore 46 by a set scrrew 47, as seen in FIG. 4. The inner end of the pin 44 has a conically-shaped recess 48 formed so as to precisely position the element 42 with its center 42a on the axis 36. Note from FIG. 3 that the element 42 is not restrained by the upper wall 40b of the cut out 40.

It should be noted also that the outer face of the frame portion 16a and the inner face of the guide 32 are smoothly flush to be precisely mated. Preferably, these surfaces are perpendicular to the axis 36.

Each condyle 42 is supported on a post or pedestal 50 which has a relatively small diameter at the upper end and then flares outwardly below the guides to a cylindrical base 50a having a diameter somewhat larger than the socket 14 formed in the lower frame. The pedestal further has a generally cylindrical lower end 50b, which may be seen from FIG. 3 to have a diameter considerably smaller than that of the socket 14. It may also be seen from FIG. 3 that the lower surface 50c of the pedestal is spaced from the bottom of the socket. Also, the upper surface 10h of the frame portion 10g surrounding the socket is spaced from the lower surface 50d of the pedestal base 50a.

In accordance with the invention, the pedestal is held in the lower frame by a quick-setting bonding material 60, such as a resin or other suitable material, which will rigidly and permanently secure the pedestals to the lower frame. The lower cylindrical end of the pedestal is formed with an annular recess 50e, and bonding material extends into this recess to further strengthen the connection.

From the foregoing, the method of the invention is probably apparent, but the steps will be summarized.

The fixtures 32 are mounted in the upper frame portion 16a and the condylar elements 42, attached to the pedestals 50, are captured within the fixtures by means of the retaining pins 44. The alignment block 20 is secured to the lower frame by the set screw and properly aligned thereon by the dowels 15. The resin or other bonding material 60 is then positioned or injected into the sockets 14. The upper frame 16 is then mounted on the alignment block 20; and as the frame is being moved into position, the lower ends of the pedestals are inserted into the sockets 14 displacing some of the resin out the upper end of the socket. With the upper frame securely attached to the upper surface of the alignment block, the pedestals are suspended in a manner illustrated in FIG. 3. Since the condylar elements 42 are spherical, the pedestals can be moved a limited amount about the condylar elements without engaging the socket walls. The exact positioning of the lower ends is not critical since it is the positioning of the condylar elements 42 which is important; and they are captured by the upper frame. It is important that the lower end of a pedestal not be restrained by the socket wall so that the accuracy of the mounting by the fixtures 32 and guide pins 44 is not adversely affected. With this approach neither the sockets 14 or the frame surface 10h need by precisely machined.

The bonding material is preferably in a flowable but somewhat thick form when it is placed into the socket 14, so that when a portion of the material is displaced upwardly by the end of the pedestal, it will remain between the frame surface 10h and the lower surface 50d of the pedestal base 50a, as shown in FIG. 3. The bonding material preferably sets within a short interval, and during this time, the frames remain mounted on the alignment block and the condylar elements remain captured in the upper frame guide fixtures. Once the bonding material is set or hardened, the retainer pins 44 may be retracted and the frames disconnected from the alignment block.

FIG. 5 illustrates a slight modification of the guide structure of the upper frame. In that arrangement, fixtures 62 are formed with a conical recess 64 on the inner wall 62a of the space 66. This, in cooperation with the pin recess 48, more positively aligns the condylar element 42 within the fixtures of the upper frame.

To permit separation of the fixtures 62 from the condylar elements 42, there is provided a flat U-shaped shim 70 as seen in FIGS. 5 and 6. The shim 70 fits between the inner face of the fixture 62 and the outer face of the upper frame 16a. It is necessary that the shim be removed to permit the fixture 62 to be moved closer to the upper frame 16a so as to allow the condylar elements to be removed from the fixtures 62. To accommodate this inward movement, it is, of course, also necessary to retract the retainer pins 72.

In the arrangement of FIG. 5, the retainer pins 72 have a slightly modified construction from that illustrated in FIG. 4. More specifically, retainer pins 72 have an inner cylindrical guide portion 72a within the bore in the fixture 62. A larger diameter central portion 72b is threaded on its exterior to mate with threads 74 formed in the outer end of the bore in the fixture 62. With this arrangement, the retainer pins 72 can be threaded inwardly or outwardly to engage or disengage the condylar element 42. It should be noted that the inner cylindrical guide portion 72a concentrically aligns the pin 72 within the bore of the guide 62, and the threads 74 and 72b merely move the pin axially in or out. To more positively hold the pin in a selected axial position, a set screw 76 may also be provided.

Figure 8:
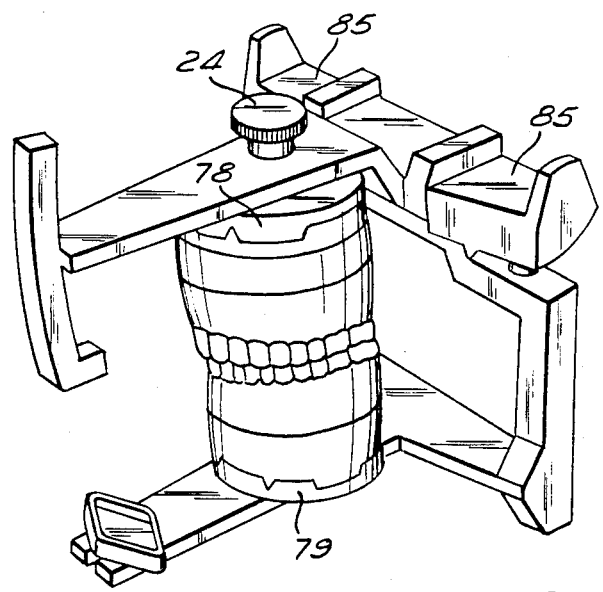
FIG. 8 is a perspective view illustrating the manner in which the dental casts of FIG. 7 are mounted on the articulator of FIGS. 1 and 2 after the alignment block and guide fixtures have been removed and replaced by the operative guide blocks and the dental casts and mounting plates.
Figure 9:
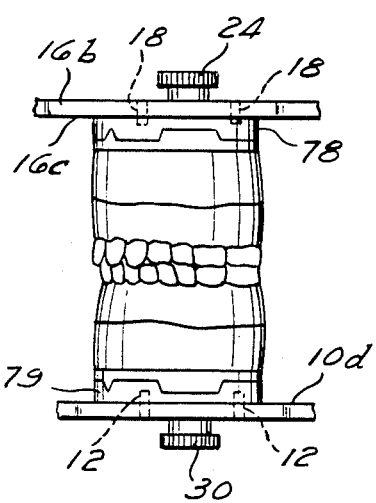
FIG. 9 is a side elevational view of a portion of FIG. 8.

To appreciate the importance of the accurate positioning of the condylar elements 42 and the relationship between the upper and lower frames, consider now the use of an articulator made in accordance with the method of the invention. The alignment block 20 is removed and replaced by upper and lower dental cast mounting plates 78 and 79, which have precisely machined surfaces that mate with the surfaces 10d and 16c on the articulator frames as seen in FIGS. 8 and 9. Also, the dowels 12 on the lower frame mate with the lower mounting plate 79 and the dowels 18 mate with recesses in the upper mounting plate 78. These plates 78 and 79 are held on the articulator frames by the screws 24 or 30 or by separate screws (not shown).

Dental casts or models 80 and 81 of a patient's upper and lower teeth are attached to the mounting plates in a known manner. Specifically, plaster portions 82 and 83 cooperate with the dental casts 80 and 81 and the mounting plates 78 and 79 to position the casts on the articulator frames.

The dental casts are carefully and accurately initially connected to the mounting plates. In the arrangement shown, the screws 24 and 30 thread into inserts 84 in the plaster 82 an 83. Further details of this mounting may be seen in U.S. Pat. No. 4,600,385. In another approach (not shown), the plaster is permanently attached to the plate. They are either kept with the particular mounting plates or if the mounting plates are sufficiently accurate, the casts are stored without the mounting plates as shown in FIG. 7, and then mounted to the mounting plates when they are to be used. The preferred approach is that illustrated wherein the dental casts remain with the articulator frames, and a dental cast is attached to the mounting plates by threading the mounting screw into a mounting knob 84 embedded in the plaster connected to the cast. The plaster is formed with ribs 82a and 83a which mate with corresponding grooves on the mounting plate. The precise nature of this mating can be seen in FIG. 9.

The fixtures 32 are replaced by guides 84 and 85 having recesses (not shown) formed therein for receiving the condylar elements. The instrument may then be used to simulate jaw movements corresponding to the movements of the patient's dental casts due to the hinging and sliding action of the articulator frames.

From the foregoing, it may be recognized that the accuracy of the simulated movement is dependent upon the accuracy of the hinge axis as formed by the condylar elements and the corresponding relationship between the guides 84 and 85 on the upper frame and the mounting of the upper frame with respect to the lower frame. The method of the invention not only provides this necessary accuracy, but it does it in an improved manner that minimizes the amount of machining required. More specifically, it eliminates the need to precisely attempt to locate the pedestals in and on the lower frame. Accurately mounting the lower ends of the pedestals is an indirect method of obtaining the desired accuracy in that it is the position of the condylar elements in relation to the upper frame which is of controlling importance.

What is claimed is:

1. A method of making interchangeable dental articulator frames comprising:
    forming a pair of spaced sockets in the upper surface of a vertical support of the lower frame of a dental articulator, each socket being adapted to receive the lower end of a pedestal having a condylar element on its upper end, said element being adapted to simulate the condyles of a jaw, and to cooperate with a guide on the upper frame of a dental articulator, each of said sockets being formed larger than said pedestal lower end;

injecting bonding material in each of said sockets, with said material being initially in flowable form but being adapted to harden fairly quickly;

positioning an upper frame of a dental articulator in a predetermined precise position with respect to said loer frame and with a pair of said elements captured in known precise relation in fixtures on said upper frame, and with the lower ends of said pedestals extending into said sockets; and holding said frames in said position until the bonding material has hardened thereby capturing the lower ends of said pedestal with said elements, in a predetermined known precise relation.

2. The method of claim 1 including the step of capturing said elements in said upper frame in said known precise relation before the pedestals are attached to said lower frame, and the centers of said elements define a line which extends through a known axis that represents the hinge axis of the articulator.

3. The method of claim 1, wherein each of said condylar elements has a spherical shape and is captured within said upper frame in a manner to permit the lower end of each of said pedestals to have limited movement within its socket.

4. The method of claim 3, wherein the lower end of each pedestal is spaced from the bottom wall of its socket.

5. The method of claim 1, wherein said pedestal lower ends do not interfere in any way with said lower frame.

6. The method of claim 1, wherein said pedestals include a large base portion positioned adjacent said lower end, the base portion having a diameter larger than the diameter of the adjacent socket, and wherein said upper frame positioning step includes supporting said pedestals in a position wherein the lower surface of each of said base portions is spaced from said upper surface of said vertical support.

7. The method of claim 1, wherein said injecting step includes pouring a quick-setting resin into said sockets for use as said bonding material.

8. The method of claim 1, wherein said upper frame includes a central portion with a pair of shafts extending laterally outwardly to define a hinge axis for said articulator, said upper frame further includes a pair of fixtures mounted on said shafts, each of said fixtures having a space in which one of said condylar elements is received, said fixtures further including a clamping pin for clamping said condylar element against a wall of said fixture space, said pins being colinear with said shafts to define a hinge axis, and said method includes clamping each of said condylar elements between the inner end of a respective one of said pins and a wall of said space.

9. The method of claim 8, wherein said clamping includes clamping said element in a recess in the inner face of each pin element, said recess being located so that the center of said condylar element then lies on said axis.

10. The method of claim 9, including the step of positioning the inner face of said fixture against the outer face of each frame central portion.

11. The method of claim 9, wherein said wall of said space engaging said condylar element includes a recess for aligning said condylar element so that its center lies on said axis, and said method includes the step of positioning a shim between the inner face of said fixture and the outer face of said frame member.

12. The method of claim 11, including the step of withdrawing said pin and withdrawing said shim to allow said fixture to be moved inwardly to thereby release said condylar element and allow said upper frame to be separated from said lower frame.

13. The method of claim 1, including the step of positioning a alignment block between flat reference surfaces on each of said frames with said alignment block having upper and lower parallel surfaces, whereby portions of said upper and lower frames are held in spaced position with respect to each other.

14. A dental articulator comprising:
a lower frame having a rear upwardly extending frame member with a pair of spaced sockets formed in the upper surface of said member;
a pair of condyle support pedestals each having a lower end positioned in a respective one of said sockets but being smaller than said sockets;
a pair of condylar elements each mounted on the upper end of a respective one of said pedestals to define a hinge axis through the centers of said elements;
bonding material positioned in said socket in the space between the socket walls and said pedestal ends forming the only connecting means between the socket walls and the pedestal ends.

15. The articulator of claim 14, wherein each of said pedestals has an enlarged base adjacent said pedestal end, the base having a cross-sectional dimension larger than said socket and the lower surface of said base is spaced slightly from the upper surface of said frame member surounding said socket, and a layer of said bonding material extends between said base lower surface and the upper surface of said frame member surrounding said socket.

16. The articulator of claim 15, wherein said bonding material is initially flowable such that the pedestal ends can be inserted into the sockets with the flowable bonding material positioned therein and the pedestal ends are then movable within the bonding material, and said flowable material hardens quickly and bonds said pedestals rigidly within said sockets while the condylar elements are held in a known relation.

* * * * *